United States Patent [19]

Tennigkeit et al.

[11] Patent Number: 5,431,698
[45] Date of Patent: Jul. 11, 1995

[54] PROCESS FOR OXIDATIVE DYEING AND RE-DYEING OF HUMAN HAIR

[75] Inventors: Jürgen Tennigkeit, Seeheim; Heribert Lorenz, Gross-Bieberau; Guenter Much, Darmstadt, all of Germany

[73] Assignee: Goldwell AG, Germany

[21] Appl. No.: 212,029

[22] Filed: Mar. 11, 1994

[30] Foreign Application Priority Data

Apr. 30, 1993 [DE] Germany .................. 43 14 253.2

[51] Int. Cl.⁶ ............................................. A61K 7/13
[52] U.S. Cl. ............................................. 8/408; 8/406; 8/435; 8/504
[58] Field of Search ............... 8/405, 406, 408, 435, 8/485, 504

[56] References Cited

U.S. PATENT DOCUMENTS

| | | | |
|---|---|---|---|
| 4,992,077 | 2/1991 | Tennigkeit et al. | 8/406 |
| 5,006,127 | 4/1991 | Tennigkeit et al. | 8/406 |
| 5,053,051 | 10/1991 | Tennigkeit et al. | 8/406 |

Primary Examiner—Paul Lieberman
Assistant Examiner—Caroline L. Dusheck

[57] ABSTRACT

A new multi-step process for dyeing human hair achieving improved coverage and gentle treatment of the hair and, in addition, allowing the production of numerous hair dye shades using a relatively small number of hair dye compositions, which process consists of the following steps:

a) Application of an alkaline oxidation hair dye composition comprising at least one developing substance and at least one coupling substance as well as an oxidizing agent mainly onto that part of the human hair which is next to the scalp, whereby the mixture is adjusted to the hair shade desired for the total dyeing result;

b) rinsing and shampooing of the hair after completed processing of the dyeing composition;

c) application of an acidic oxidation hair dye composition comprising at least one developing and at least one coupling agent as well as an oxidizing agent, to the total hair, and d) rinsing of the hair after complete processing of the hair dye.

8 Claims, No Drawings

PROCESS FOR OXIDATIVE DYEING AND RE-DYEING OF HUMAN HAIR

This invention relates to a new process for oxidative dyeing of human hair and the re-dyeing of previously dyed hair giving not only a milder treatment to the hair than customary processes but also imparts an improved coverage of the hair color; moreover the invention allows to produce a multitude of desired dyeing shades from only a small selection of basic hair dye compositions.

The most common way of hair dyeing is still a process using oxidation hair dyes which are mixed with an oxidizing composition, particularly on the basis of diluted hydrogen peroxide, immediately before application of the mixture onto the hair.

The pH-value of these ready-to-use compositions is normally in the alkaline range, especially between about pH 9 and about 10.

This kind of alkaline treatment, especially in cases of frequent repetition of the dyeing process, damages the hair structure particularly when the hair was previously impaired. After the dyeing process, such porous hair usually possesses poor colorfastness.

It has already been suggested to overcome these disadvantages of customary hair dyeing by departing from the practice described above and by using a dyeing composition having a pH-value in the slightly acidic range between about 5.9 and 6.9, instead of an alkaline composition of oxidation hair dye and oxidizing agent.

Such compositions, as they are disclosed in German Patent Applications Nos. 35 30 270, 36 28 397, and 36 28 398, in fact proved to be less damaging to the hair than alkaline products.

In certain cases, i.e. with particular hair dyeing shades, the coverage of these improved compositions still is not quite satisfactory.

The present invention, therefore, starts from the problem to overcome such disadvantages.

The solution of this problem is the development of a new process for oxidative dyeing and re-dyeing of human hair comprising the following steps:

a) Application of a composition having an alkaline pH-value, comprising an oxidation dye composition containing at least one developing and at least one coupling substance as well as an oxidizing agent, mainly to the part of the hair next to the scalp, i e , the "hair line" wherein the dye mixture is already adjusted to the shade desired for the total hair;

b) rinsing and shampooing of the hair after processing of the hair dye;

c) application of an acidic oxidation hair dye composition to the total hair comprising at least one developing and at least one coupling agent as well as an oxidizing agent; and d) rinsing of the hair after completed hair dye processing.

This specific procedure not only allows gentle hair dyeing and an excellent color coverage but, due to the use of special dye mixtures adjusted to the final shade desired by the user, . . . also enables an application of the anticipated final shade already within the first dyeing step to be developed in the second step by the application of suitable dyestuff premixes without the need to store the variety of all individual compositions required for the specific shades.

Thus, this process is an essential simplification for both, the hair dye producer and the hairdresser.

According to a preferred embodiment of the invention, the processing time of the dye compound within the second stage of the treatment is about 10 to about 30 minutes, preferably about 15 to about 20 minutes shorter compared to the first stage of the treatment, where it lasts about 20 to 50, preferably about 30 to 45 minutes. These intervals may be reduced by about a quarter to half by application of heat, preferably about 30° to 50° C., particularly about 40 ° C.

In case the dyeing process is a first-time hair dyeing, it is advisable to apply the alkaline dyeing treatment over the whole length of the hair, however, paying special attention to the treatment of the hair line.

Both, the alkaline oxidation hair dye compositions used in the first step of treatment, i.e. mainly at the so-called "hair line" which is the part of the hair shaft located next to the scalp, and the acidic oxidation hair dye compositions used in the second step, containing each at least one developing and one coupling substance as well as an oxidizing agent, are known per se.

In the Examples shown in the present specification, p-toluylenediamine sulfate is used as the developing agent, while resorcinol, 3-aminophenol, 4-aminophenol, 2-methylresorcinol are possible coupling agents which may be used.

With the regard to the alkaline mixtures having a pH-value between about 8 and 10.5, preferably 9 and 10, most preferred about 9.5, reference is made to the relevant standard literature describing the state of the art, e.g., the monography of K. Schrader, "Grundlagen und Rezepturen der Kosmetika", 2rid Ed., pp. 784 to 804 (1989); the products disclosed therein are also suitable within the scope of the process according to the invention, as well as the other developing and coupling substances or shade modifiers known from the wide range of prior art.

The same applies to the acidic hair dye compositions, adjusted to a pH-value from about 5 to 7, particularly to about 5.5 to 6.9, preferably 6.7 to 6.8, as they are e.g. known from the German Patent Applications mentioned above.

A diluted hydrogen peroxide solution, emulsion or gel is predominantly used as oxidizing agent, but it is also possible though less usual to use other peroxides such as urea peroxide, melamin peroxide, etc. in an appropriate stoichiometric dosage.

The compositions may be used as solutions, creams, pastes, gels, aerosols, etc.

The following examples illustrate the invention:

EXAMPLE 1

20 ml of an alkaline oxidation hair dye composition comprising

| 16.0% | (by wt.) | Cetylstearyl alcohol |
|---|---|---|
| 2.8 | | Stearic acid monoethanolamide |
| 2.8 | | Coconut monoethanolamide |
| 1.5 | | Propyleneglycol mono/distearate |
| 3.0 | | Oleic acid |
| 2.5 | | 1,2-Propyleneglycol |
| 0.5 | | Sodium laurylsulfate |
| 0.5 | | Complexing agent |
| 0.5 | | Ammonium chloride |
| 1.0 | | Sodium sulfite |
| 10.0 | | Monoethanolamine |
| 2.5 | | Protein hydrolyzate |
| 0.2 | | Perfume |

-continued

| | |
|---|---|
| 2.6 | p-Toluylenediamine sulfate |
| 1.0 | Resorcinol |
| 0.2 | 3-Aminophenol |
| 0.03 | o-Chloro-p-phenylenediamine |
| 0.03 | 4-Hydroxyethyl-2-aminoanisole sulfate |
| @ 100.00 | Water, | are mixed with 5 ml of a compound comprising

| | | |
|---|---|---|
| 16.0% | (by wt.) | Cetylstearyl alcohol |
| 2.8 | | Stearic acid monoethanolamide |
| 2.8 | | Coconut monoethanolamide |
| 1.5 | | Propyleneglycol mono/distearate |
| 3.0 | | Oleic acid |
| 2.5 | | 1,2-Propyleneglycol |
| 0.5 | | Sodium laurylsulfate |
| 0.5 | | Complexing agent |
| 0.5 | | Ammonium chloride |
| 1.0 | | Sodium sulfite |
| 8.7 | | Monoethanolamine |
| 2.5 | | Protein hydrolyzate |
| 0.2 | | Perfume |
| 0.6 | | p-Toluylenediamine sulfate |
| 0.4 | | p-Amino-o-cresol |
| 0.5 | | 4-Aminophenol |
| @ 100.00 | | Water, | and
ml of 6% aqueous hydrogen peroxide solution.

The composition obtained thereby has a pH-value of 9.5. It is applied onto the hair line of a volunteer and worked in well with a comb. After 45 minutes the hair is rinsed, shampooed, and then the total hair is treated with a composition prepared by admixture of: 40 ml of a 2% aqueous hydrogen peroxide solution with ml of a hair dye composition having a pH-value of 6.8, comprising:

| | | |
|---|---|---|
| 9.0% | (by wt.) | Cetylstearylalcohol |
| 2.0 | | Protein hydrolyzate |
| 1.0 | | Oleic acid |
| 1.6 | | Stearic acid monoethanolamide |
| 2.6 | | Coconut monoethanolamide |
| 1.5 | | Sodium laurylsulfate |
| 0.3 | | Sodium sulfite |
| 0.3 | | Sodium hydroxide |
| 0.3 | | Ammonium chloride |
| 0.5 | | Hydroxyethyl cellulose |
| 0.1 | | Manganese (II) oxide |
| 0.2 | | Complexing agent |
| 0.3 | | Perfume |
| 0.6 | | HC Red No. 3 |
| 0.4 | | p-Toluylenediamine sulfate |
| 0.3 | | 4-Aminophenol |
| 0.3 | | 4-Amino-2-hydroxytoluene |
| 0.1 | | Sodium picramate |
| 0.06 | | 3-Aminophenol |
| 0.03 | | Resorcinol |
| @ 100.00 | | Water. |

After 20 minutes processing, the hair is rinsed, shampooed and dried.

The result is an even, expressive teak brown hair shade.

EXAMPLE 2

20 ml of an alkaline oxidation hair dye composition comprising:

| | | |
|---|---|---|
| 16.0% | (by wt.) | Cetylstearyl alcohol |
| 2.8 | | Stearic acid monoethanolamide |
| 2.8 | | Coconut monoethanolamide |
| 1.5 | | Propyleneglycol mono/distearate |
| 3.0 | | Oleic acid |
| 2.5 | | 1,2-Propyleneglycol |
| 0.5 | | Sodium laurylsulfate |
| 0.5 | | Complexing agent |
| 0.5 | | Ammonium chloride |
| 1.0 | | Sodium sulfite |
| 12.2 | | Monoethanolamine |
| 2.5 | | Protein hydrolyzate |
| 0.2 | | Perfume |
| 1.9 | | p-Toluylenediamine sulfate |
| 0.75 | | Resorcinol |
| 0.1 | | 3-Aminophenol |
| 0.07 | | 2-Methylresorcinol |
| @ 100.00 | | Water, | are mixed with 5 ml of an alkaline oxidation dye composition comprising:

| | | |
|---|---|---|
| 16.0% | (by wt.) | Cetylstearyl alcohol |
| 2.8 | | Stearic acid monoethanolamide |
| 2.8 | | Coconut monoethanolamide |
| 1.5 | | Propyleneglycol mono/distearate |
| 3.0 | | Oleic acid |
| 2.5 | | 1,2-Propyleneglycol |
| 0.5 | | Sodium laurylsulfate |
| 0.5 | | Complexing agent |
| 0.5 | | Ammonium chloride |
| 0.8 | | Sodium sulfite |
| 8.7 | | Monoethanolamine |
| 2.5 | | Protein hydrolyzate |
| 0.2 | | Perfume |
| 0.5 | | 4-Aminophenol |
| 0.1 | | p-Amino-o-cresol |
| 0.1 | | 2-Methylresorcinol |
| @ 100.00 | | Water, | and 50 ml of 6% hydrogen peroxide solution.

The mixture obtained thereby has a pH-value of 9.5; it is applied onto the hair line of a client and thoroughly worked in with a comb. After 35 minutes of processing, the hair is rinsed, shampooed and thereafter the total hair is treated with a composition prepared by mixing 40 ml of a 2% aqueous hydrogen peroxide solution and 20 ml of a dyeing composition having a pH-value of 6.8, comprising:

| | | |
|---|---|---|
| 9.0% | (by wt.) | Cetylstearylalcohol |
| 2.0 | | Protein hydrolyzate |
| 1.6 | | Stearic acid monoethanolamide |
| 2.2 | | Coconut monoethanolamide |
| 1.5 | | Sodium laurylsulfate |
| 1.0 | | Oleic acid |
| 0.5 | | Hydroxyethyl cellulose |
| 0.3 | | Sodium sulfite |
| 0.3 | | Sodium hydroxide |
| 0.2 | | Complexing agent |
| 0.3 | | Ammonium chloride |
| 0.2 | | Perfume |
| 0.1 | | Manganese (II) oxide |
| 0.6 | | p-Toluylenediamine sulfate |
| 0.1 | | 4-Aminophenol |
| 0.1 | | 4-Amino-2-hydroxytoluene |
| 0.1 | | 3-Aminophenol |
| 0.2 | | Sodium picramate |
| 0.05 | | Resorcinol |
| @ 100.00 | | Water. |

After 15 minutes processing, the hair is rinsed, shampooed and dried.

The result is an even, expressive golden brown hair shade.

EXAMPLE 3

20 ml of an alkaline ozidation hair dye composition comprising

| 16.0% | (by wt.) | Cetylstearyl alcohol |
|---|---|---|
| 2.8 | | Stearic acid monoethanolamide |
| 2.8 | | Coconut monoethanolamide |
| 1.5 | | Propyleneglycol mono/distearate |
| 3.0 | | Oleic acid |
| 2.5 | | 1,2-Propyleneglycol |
| 0.5 | | Sodium laurylsulfate |
| 0.5 | | Complexing agent |
| 0.5 | | Ammonium chloride |
| 0.8 | | Sodium sulfite |
| 11.5 | | Monoethanolamine |
| 2.5 | | Protein hydrolyzate |
| 0.2 | | Perfume |
| 1.0 | | p-Toluylenediamine sulfate |
| 0.4 | | Resorcinol |
| 0.05 | | 3-Aminophenol |
| 0.1 | | 2-Methylresorcinol |
| @ 100.00 | | Water, | are mixed with 5 ml of an oxidation hair dye composition comprising:

| 16.0% | (by wt.) | Cetylstearyl alcohol |
|---|---|---|
| 2.8 | | Stearic acid monoethanolamide |
| 2.8 | | Coconut monoethanolamide |
| 1.5 | | Propyleneglycol mono/distearate |
| 3.0 | | Oleic acid |
| 2.5 | | 1,2-Propyleneglycol |
| 0.5 | | Sodium laurylsulfate |
| 0.5 | | Complexing agent |
| 0.5 | | Ammonium chloride |
| 0.8 | | Sodium sulfite |
| 9.0 | | Monoethanolamine |
| 2.5 | | Protein hydrolyzate |
| 0.2 | | Perfume |
| 0.25 | | p-Toluylenediamine sulfate |
| 0.08 | | Resorcinol |
| 0.02 | | 3-Aminophenol |
| 0.06 | | o-Chloro-p-phenylene diamine |
| 0.09 | | 4-Hydroxyethyl-2-aminoanisole sulfate |
| @ 100.00 | | Water, | and 50 ml of 6% hydrogen peroxide solution.

The mixture obtained has a pH-value of 9.5; it is applied onto the hair line of a client and worked in thoroughly with a comb.

After 30 minutes processing at about 45° C., the hair is rinsed, shampooed, and thereafter, the total hair is treated with a composition made up from: 40 ml of a 2% hydrogen peroxide solution and 20 ml of a hair dye composition comprising:

| 9.0% | (by wt.) | Cetylstearyl alcohol |
|---|---|---|
| 2.0 | | Protein hydrolyzate |
| 1.6 | | Stearic acid monoethanolamide |
| 2.2 | | Coconut monoethanolamide |
| 1.5 | | Sodium laurylsulfate |
| 1.0 | | Oleic acid |
| 0.5 | | Hydroxyethyl cellulose |
| 0.3 | | Sodium sulfite |
| 0.3 | | Sodium hydroxide |
| 0.2 | | Complexing agent |
| 0.2 | | Perfume |
| 0.3 | | Ammonium chloride |
| 0.12 | | Manganese (II) oxide |
| 0.45 | | p-Toluylenediamine sulfate |
| 0.5 | | 4-Aminophenol |
| 0.01 | | 4-Amino-2-hydroxytoluene |
| 0.02 | | Resorcinol |
| 0.03 | | 3-Aminophenol |
| 0.005 | | m-Phenylenediamine |
| @ 100.00 | | Water. |

The mixture obtained thereby has a pH-value of 6.8. After 15 minutes processing time at about 40° C., the hair is rinsed, shampooed and dried.

The result is an even and expressive natural medium ash blonde hair shade.

EXAMPLE 4

25 ml of an alkaline oxidation hair dye composition comprising

| 16.0% | (by wt.) | Cetylstearyl alcohol |
|---|---|---|
| 2.8 | | Stearic acid monoethanolamide |
| 2.8 | | Coconut monoethanolamide |
| 1.5 | | Propyleneglycol mono/distearate |
| 3.0 | | Oleic acid |
| 2.5 | | 1,2-Propyleneglycol |
| 0.5 | | Sodium laurylsulfate |
| 0.5 | | Complexing agent |
| 0.5 | | Ammonium chloride |
| 1.0 | | Sodium sulfite |
| 11.5 | | Monoethanolamine |
| 2.5 | | Protein hydrolyzate |
| 0.2 | | Perfume |
| 0.8 | | p-Toluylenediamine sulfate |
| 0.3 | | Resorcinol |
| 0.04 | | 3-Aminophenol |
| 0.1 | | 2-Methylresorcinol |
| @ 100.00 | | Water, | are mixed with 50 ml of a 6% aqueous hydrogen peroxide solution.

The mixture obtained thereby has a pH-value of 9.5; it is applied onto the hair line of a client and thoroughly worked in with a comb. After 40 minutes processing the hair is rinsed, shampooed, and thereafter the total hair is treated with a composition made up from 40 ml of 6% aqueous hydrogen peroxide solution, and 20 ml of a hair dye composition comprising:

| 9.0% | (by wt.) | Cetylstearyl alcohol |
|---|---|---|
| 2.0 | | Protein hydrolyzate |
| 1.6 | | Stearic acid monoethanolamide |
| 2.2 | | Coconut monoethanolamide |
| 1.5 | | Sodium laurylsulfate |
| 1.0 | | Oleic acid |
| 0.5 | | Hydroxyethyl cellulose |
| 0.3 | | Sodium sulfite |
| 0.2 | | Sodium hydroxide |
| 0.2 | | Complexing agents |
| 0.3 | | Ammonium chloride |
| 0.1 | | Calcium chloride |
| 0.2 | | Perfume |
| 0.3 | | p-Toluylenediamine sulfate |
| 0.07 | | 4-Aminophenol |
| 0.01 | | 4-Amino-2-hydroxytoluene |
| 0.04 | | Sodium picramate |
| 0.04 | | 3-Aminophenol |
| 0.03 | | Resorcinol |
| 0.01 | | HC Yellow No. 5 |
| @ 100.00 | | Water. |

The mixture obtained thereby has a pH-value of 6.7. After a processing time of 20 minutes at about 40° C., the hair is rinsed, shampooed and dried.

The result is an even and expressive sandy blonde hair shade.

We claim:

1. A process for oxidative dyeing and redyeing of human hair, the hair having a hair line region of a total length of the hair being in close proximity to the scalp, the process comprising the following sequential steps:
   a) application of an alkaline oxidation hair dye composition comprising at least one developing substance, at least one coupling substance, and an oxidizing agent, wherein a principal portion of the dye is applied to the hair line region, while the remaining portion of the dye is applied to the remaining hair length, the alkaline composition being adjusted to a final hair shade desired for the total length of the hair;
   b) processing of the alkaline composition on the hair, followed by rinsing and shampooing of the hair;
   c) application of an acidic oxdiation hair dye composition comprising at least one developing substance, at least one coupling substance, and an oxidizing agent, to the total length of the hair; and
   d) processing of the acidic composition on the hair, followed by rinsing of the hair.

2. Process according to claim 1, wherein the processing time of step (d) is shorter than that of step (b).

3. Process according to claim 1, wherein the processing of steps (b) and (d) is performed at about 30° to 50° C.

4. Process according to claim 2, wherein the processing of steps (b) and (d) is performed at about 30° to 50° C.

5. Process according to claim 2, wherein the processing of step (b) takes place for approximately 20 to 50 minutes, and the processing of step (d) takes place for approximately 10 to 30 minutes.

6. Process according to claim 5, wherein the processing of step (b) takes place for approximately 30 to 45 minutes, and the processing of step (d) takes place for approximately 15 to 20 minutes.

7. Process according to claim 5, wherein the processing of steps (b) and (d) is performed at about 30° to 50° C.

8. Process according to claim 6, wherein the processing of steps (b) and (d) is performed at about 30° to 50° C.

* * * * *